(12) United States Patent
Harkrider, Jr.

(10) Patent No.: US 6,328,730 B1
(45) Date of Patent: Dec. 11, 2001

(54) ENDOLUMINAL MULTI-LUMINAL SURGICAL SHEATH AND METHOD

(76) Inventor: William W. Harkrider, Jr., 118 Bayou Dr., New Iberia, LA (US) 70563

( * ) Notice: Subject to any disclaimer, the term of this patent is extended or adjusted under 35 U.S.C. 154(b) by 0 days.

(21) Appl. No.: 09/276,679

(22) Filed: Mar. 26, 1999

(51) Int. Cl.⁷ .................................................. A61M 25/00
(52) U.S. Cl. ........................ 604/523; 604/527; 600/130; 600/153
(58) Field of Search ................................... 604/523, 164, 604/171, 528, 526, 527, 264, 284; 600/128, 130, 153, 156

(56) References Cited

U.S. PATENT DOCUMENTS

| | | |
|---|---|---|
| 1,303,135 * 5/1919 | Wappler . | |
| 4,361,139 * 11/1982 | Takagi | 600/138 |
| 4,601,701 7/1986 | Mueller, Jr. . | |
| 4,668,221 * 5/1987 | Luther | 604/164 |
| 4,757,819 * 7/1988 | Yokoi et al. | 128/662.06 |
| 4,802,461 * 2/1989 | Cho | 600/108 |
| 4,838,881 6/1989 | Bennett . | |
| 4,909,798 3/1990 | Fleischhacker et al. . | |
| 4,979,496 * 12/1990 | Komi | 600/113 |
| 4,989,586 * 2/1991 | Furukawa | 600/110 |
| 5,092,857 3/1992 | Fleischhacker . | |
| 5,156,590 * 10/1992 | Vilmar | 604/4 |
| 5,195,962 * 3/1993 | Martin et al. | 604/523 |
| 5,207,648 5/1993 | Gross . | |
| 5,209,741 * 5/1993 | Spaeth . | |
| 5,217,001 * 6/1993 | Nakao et al. | 600/123 |
| 5,221,256 * 6/1993 | Mahurkar | 604/523 |
| 5,250,038 10/1993 | Melker et al. . | |
| 5,261,889 * 11/1993 | Laine et al. | 604/164 |
| 5,342,301 * 8/1994 | Saab | 604/96 |
| 5,364,377 * 11/1994 | O'Neil | 604/283 |
| 5,411,020 * 5/1995 | Ito | 600/146 |
| 5,483,951 * 1/1996 | Frassica et al. | 604/104 |
| 5,486,159 1/1996 | Mahurkar . | |
| 5,632,717 * 5/1997 | Yoon | 600/106 |
| 5,702,368 * 12/1997 | Stevens et al. | 604/171 |
| 5,741,271 * 4/1998 | Nakao et al. | 606/114 |
| 5,891,111 * 4/1999 | Ismael | 138/116 |
| 6,013,047 * 1/2000 | King | 604/22 |
| 6,077,256 * 6/2000 | Mann | 604/500 |
| 6,146,354 * 11/2000 | Beil | 604/523 |
| 6,224,585 * 5/2001 | Pfeiffer | 604/523 |

* cited by examiner

Primary Examiner—Richard K. Seidel
Assistant Examiner—Jeremy Thissell
(74) Attorney, Agent, or Firm—Carter, Ledyard & Milburn

(57) ABSTRACT

A radially non-deformable surgical access catheter with a central lumen surrounded by plural peripheral lumens, the lumens being rigidly connected to each other to provide axial stiffness for the catheter as well as rotational stiffness for the catheter so that the catheter may be rotated about its longitudinal axis to place the instruments in any of the peripheral lumens into operational proximity to preselected tissue. Methods are also disclosed.

16 Claims, 2 Drawing Sheets

ENDOLUMINAL MULTI-LUMINAL SURGICAL SHEATH AND METHOD

BACKGROUND OF THE INVENTION

Multilumen venus catheters are well known. Some such as that disclosed in the Mueller Jr. U.S. Pat. No. 4,601,701 consist of a single tube equipped with a mixing hub at the proximate end. Other multilumen venus catheters such as disclosed in the Bennett U.S. Pat. No. 4,838,881 dated Jun. 13, 1989 consist of plural tubes each having a circular cross-section, with the tubes welded together over the entire length thereof. Still others such as disclosed in the Gross U.S. Pat. No. 5,207,648 dated May 4, 1993 and the Mahurkar U.S. Pat. No. 5,486,159 dated Jan. 23, 1996 provide plural radially rigid, circular cross-section, concentric lumens or plural lumens surrounding a central reinforcing strip. Such catheters are useful only for fluids.

Surgical access catheters are also well known and are used to facilitate the introduction of surgical instruments into the body for the performance of various procedures at the distal end and protect the surrounding tissue for the trauma of multiple passages of such instruments.

Surgical catheters such as disclosed in the Melker U.S. Pat. No. 5,250,038 dated Oct. 5, 1993, provide a main and secondary lumen of significantly differing cross-section, with the main lumen being of circular cross-section for the passage of a instrument therethrough with the secondary lumen useful for fluids.

Another more versatile multilumen catheter is disclosed in the Spaeth U.S. Pat. No. 5,209,741 dated May 11, 1993 and includes an axially stiff tubular introducer with a relatively rigid funnel on the proximate end to facilitate the introduction of the introducer. Once in place proximate to the target tissue, the circular cross-section dilator may be removed from the introducer and one or more instruments introduced through the introducer, typically in the form of a circular cross-section catheter with plural lumens.

The tubular introducer is provided with axial reinforcing members sufficient to impart axial stiffness, but is radially deformable so that the flexible walls collapse around the catheter or other inserted instruments to the minimum cross-sectional configuration required by the inserted catheter or other instruments. In other embodiments, the radially deformable tubular introducer may be preformed into a non-circular cross-section to conform to a particular instrument.

While surgical catheters of this type represent a significant improvement over previously known surgical catheters, they still fail to meet the needs of physicians desiring 360° access to the tissue into which the catheter is inserted, the ability to simultaneously introduce and use plural instruments without mutual interference, to simultaneously introduce and withdraw fluids, to simultaneously use instruments and perform a fluid flush or aspiration of a vessel into which the catheter is inserted, and to avoid changes in catheter cross-section as various instruments are inserted and withdrawn.

Accordingly, it is an object of the present invention to obviate many of the deficiencies of known surgical catheters and to provide a novel surgical catheter and method.

It is another object of the present invention to provide a novel surgical catheter and method in which a constant diameter central lumen may be used to provide an axial view of the cavity in which the catheter is inserted.

It is yet another object of the present invention to provide a novel surgical catheter and method in which plural individually isolated lumens may be selectively rotated about a central lumen to thereby provide 360° access to the adjacent tissue for the instruments in each of the peripheral lumens.

It is still another object of the present invention to provide a novel surgical catheter and method in which the exterior wall may be made thinner because of the reinforcement provided by the central lumen of the catheter.

It is yet still another object of the present invention to provide a novel surgical catheter and method in which the central lumen, desirably axially centered within the catheter for axial viewing, may be offset to provide selective viewing of the side walls of a vessel.

It is a further object of the present invention to provide a novel surgical catheter and method in which space is provided between the central lumen and the peripheral lumens for use in extracting fluids and tissue from within the catheter.

It is yet a further object of the present invention to provide a novel surgical catheter and method which may be flexed without kinking, which has sufficient axial stiffness to facilitate insertion, and which is not laterally deformable by the pressure of the tissue into which inserted.

It is still a further object of the present invention to provide a novel surgical catheter and method which will retain its size and shape as well as the relative orientation of the lumens from the proximate end to the distal end, reducing trauma to the surrounding tissue from multiple passages of instruments and the like therethrough.

It is still a further object of the present invention to provide a novel surgical catheter and method in which the size, shape and relative location of the various lumens may be selectively varied to accommodate the optics and instruments of a specific surgical procedure, and through which either optics or instruments may be selectively inserted.

It is yet still a further object of the present invention to provide a novel surgical catheter and method for the introduction of a second multilumen catheter through a main vessel in which the second catheter is inserted into and out of a port lumen of the first catheter into a branch vessel to perform surgical procedures therein.

These and many other objects and advantages of the present invention will be readily apparent to one skilled in the art to which the invention pertains from a perusal of the claims, the appended drawings, and the following detailed description of the preferred embodiments.

DESCRIPTION OF PREFERRED EMBODIMENTS

Figures 1, 2:
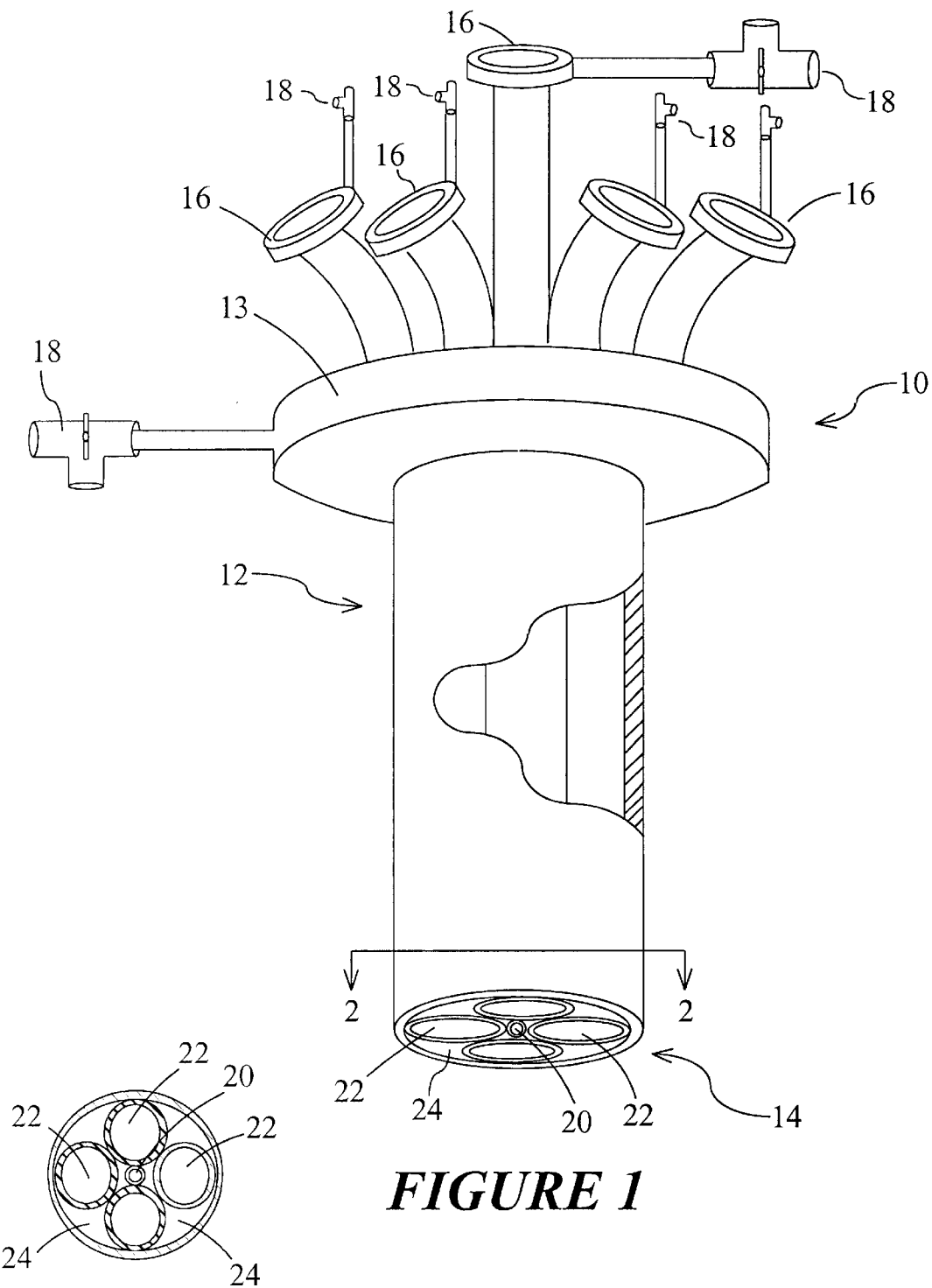
FIG. 1 is a pictorial illustration of one embodiment of the multilumen catheter of the present invention in partial section.
FIG. 2 is a section taken through lines 2—2 of the catheter of FIG. 1.
Figure 3:
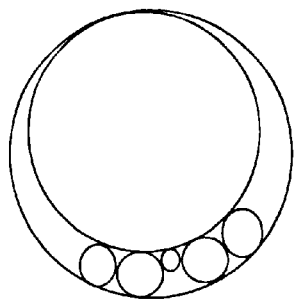
FIG. 3 is a cross-section of a second embodiment of the catheter of the present invention.
Figure 4:
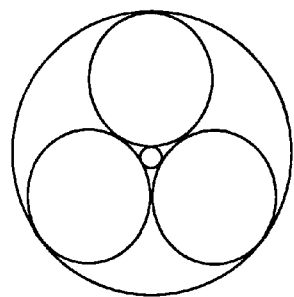
FIG. 4 is a cross-section of a third embodiment of the catheter of the present invention.

With reference to the embodiment of the catheter of FIG. 1 and FIG. 2, the proximate end 10 of the catheter is adapted to remain external of the patient with an elongated cylindrical section or endoluminal sheath 12 extending to a distal end 14 adapted to be inserted into the patient. The cylindrical section 12 is foreshortened in FIG. 1 for convenience only, but may be two meters in length.

Figure 5:
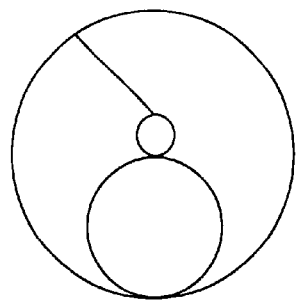
FIG. 5 is a cross-section of a fourth embodiment of the catheter of the present invention.
Figure 6:
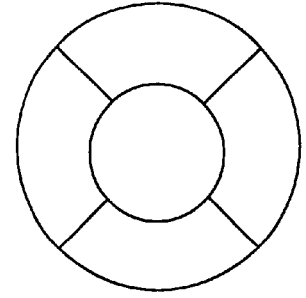
FIG. 6 is a cross-section of a fifth embodiment of the catheter of the present invention.
Figure 7:
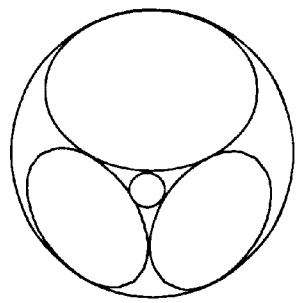
FIG. 7 is a cross-section of a sixth embodiment of the catheter of the present invention.
Figure 8:
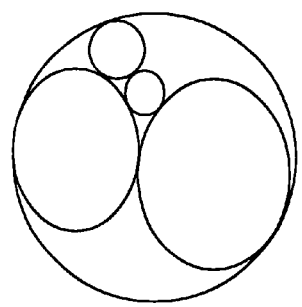
FIG. 8 is a cross-section of a seventh embodiment of the catheter of the present invention.

As shown in FIG. 1, the proximal end 10 includes a central hub 13 which may be used to provide a adjunctive access to the space 24 illustrated in FIG. 2 between the lumens, and which may also be equipped with a hemostatic valve 16 (not shown). However, and as shown in FIG. 5 and FIG. 6, there may not be spaces between the lumens and the need for a hub obviated.

Each of the lumens at the proximate extracorporeal end 10 may be provided with a suitable conventional hemostatic valve 16 with a suitable conventional three way stopcock or fluid port 18. As may be seen at the distal end 14 of the catheter in FIG. 1 and in the cross-section of FIG. 2, the interior of the catheter may contain over its length comprise a relatively small central lumen 20, and four cylindrical cross-section lumens 22 of approximately the same diameter.

Because the five lumens 20, 22 in the catheter of FIGS. 1 and 2 do not occupy the entirety of the interior of the catheter, the walls of the lumens 20, 22 and the wall of the catheter define a longitudinal passage 24 through the catheter. A suitable conventional hemostatic valve 16 and three way stopcock 18 may be provided for each of the spaces 24 within the catheter which is not within one of the peripheral lumens.

Each of the lumens 20, 22 are open at the distal end and any number of conventional instruments of suitable size may be inserted through a selected lumen and out of the distal end thereof to provide access to the tissue of the patient in a conventional manner.

The catheter intermediate the proximate end 10 and the distal end 14 is desirably a thin wall tube of circular cross-section. The thinness of the wall provides flexibility but buckling is prevented by the lumens in the central core. These lumens are desirably rigidly secured to each other and the interior wall of the catheter and add sufficient rigidity to permit insertion of the catheter into a blood vessel, body cavity or lumen of other organs of the patient.

This rigidity also provides the ability to rotate the entire catheter about its longitudinal axis from the proximate end without changing the axial length of the catheter and thus displacement of the distal end from a desired location within the patient. The resistance to rotational deformity of the catheter is also sufficient to avoid any significant time lag from proximal to distal, so that the change in position at the distal end may immediately reflect the control of the physician at the proximate end.

The overall length of the catheter will, of course, be dependant upon the target tissue or organ, typically from about 50 mm to about 500 mm, but as long as 2,000 mm for certain procedures. The number and size of the peripheral lumens may also vary with a total endoluminal sheath diameter from about 1 mm to about 20 mm.

The material of the endoluminal sheath and the lumens may be any suitable conventional material such as nylon, polyvinyl chloride or polyethylene, or a blend thereof. Alternatively, it may be constructed by heat shrinking a plastic film over a cylindrical wire or plastic mesh of sufficient strength to resist deformation. It is important that the endoluminal sheath not radially collapse under external pressure, but great strength against outward pressure may not be required.

The catheter of the present invention may be inserted through any suitable conventional hemostasis valve, e.g., such as disclosed in the Fleischhacker et al U.S. Pat. No. 4,909,798 dated Mar. 20, 1990 of the Fleischhacker U.S. Pat. No. 5,092,857 dated Mar. 3, 1992.

In the preferred embodiment of FIG. 1, the central lumen 20 may be used to provide guide wire access in placing the catheter. Once in place, the guide wire may be withdrawn and the central lumen used for other instruments. It is a significant advantage of the catheter of the present invention that any lumen may be selected for the optics, and that the position of the optics once inserted can be controlled to facilitate the selection of the view, e.g., down the axis of the catheter, and maintained in the selected position or rotated with the catheter to vary the view. As will be appreciated, insertion of the optics through a peripheral lumen will provide a different view of the vessel in which the catheter is inserted than will insertion of the optics through a central lumen, and it may be desirable in a particular procedure to use different lumens for both optics and instruments at different times in the procedure.

Another significant advantage is the 360 degree access to tissue. Consider for example, that an instrument has been inserted into one of the peripheral lumens and the physician finds that the instrument is adjacent a wall of a blood vessel where the instrument is not needed and diametrically opposite a wall where it is needed. In this event, the physician may simply rotate the catheter, and the lumen containing the instrument may rotated into position adjacent the opposite wall of the vessel.

The isolation of the lumens from each other insures that the instruments inserted therein do not become entangled either when inserted or removed, or the rotation of the catheter.

The space between lumens is desirably used to introduce and extract fluids. Consider for example that a balloon catheter has been introduced through one of the lumens into a blood vessel and inflated to provide a distal seal of the vessel. A saline solution may then be introduced through one of these spaces into the vessel to facilitate viewing of the vessel, and the simultaneous introduction of a fluid in one of the spaces and withdrawal of the fluid from another one of the spaces provides a fluid flow mechanism for flushing severed tissue from the vessel without necessity of grabbing the tissue with an instrument and withdrawing the instrument from the catheter.

Other exemplary configurations of the catheter of the present invention are shown in FIGS. 3 through 8. All may be constructed in any suitable conventional way, or in the manner described herein, with the various spaces having sizes and shapes designed to accommodate specific optics/ instruments or specific procedures.

For example, the present invention may be used in connection with blood vessels in the leg, abdomen, heart, neck and brain from inside the vessels. Applications include the removal of stents and stent grafts which have failed as well as the placement of new grafts within the vessel and the securing of the graphs to the vessel wall by suture techniques.

While preferred embodiments of the present invention have been described, it is to be understood that the embodiments described are illustrative only and the scope of the invention is to be defined solely by the appended claims when accorded a full range of equivalence, many variations and modifications naturally occurring to those of skill in the art from a perusal hereof.

What is claimed is:

1. An elongated, generally tubular, multilumen surgical catheter comprising in cross-section:
   an outer sheath of generally circular cross-section, said sheath being flexible;
   a central tube defining a central lumen of generally circular cross-section;
   a plurality of peripheral generally cylindrical lumens defined in part by the interior wall of said outer sheath and the exterior wall of said central lumen, each of said peripheral lumens being isolated from each of the other of said lumens.

2. The multilumen catheter of claim 1 wherein said central lumen and said outer sheath are substantially coaxial.

3. The multilumen catheter of claim 1 wherein said central lumen, said outer sheath, and said peripheral lumens define plural axial passageways within the catheter.

4. An elongated, generally tubular, multilumen surgical catheter comprising in cross-section an outer sheath, a central lumen, and a plurality of peripheral lumens radially intermediate said outer sheath and said central lumen, each of said lumens being isolated from each of the other of said lumens, each of said peripheral lumens being defined at least in part by at least one of (i) said sheath, (ii) a wall defining said central lumen and (iii) a wall defining another of said plural peripheral lumen,
   said catheter being of sufficient axial stiffness to permit insertion into a patient, being sufficiently flexible to permit following a blood vessel when inserted therein and having sufficient resistance to twisting so that the distal end of the catheter may be rotated about the longitudinal axis of the catheter from the proximate end thereof to selectively position any peripheral lumen with respect to tissue at the distal end thereof.

5. The surgical catheter of claim 4 wherein said sheath is comprised of one or more of nylon, polyvinyl chloride and polyethylene.

6. The surgical catheter of claim 4 wherein said sheath is between about 50 mm and about 2000 mm in length.

7. The surgical catheter of claim 6 wherein said sheath is between about 50 mm and about 500 mm in length.

8. The surgical catheter of claim 4 wherein said sheath comprises a layer of a heat shrinkable plastic over a rigid mesh.

9. The surgical catheter of claim 4 wherein said sheath is between about 1 mm and about 20 mm in diameter.

10. The surgical catheter of claim 4 wherein said lumens extend to the distal end of said catheter.

11. The method of performing a surgical procedure in a branch vessel comprising the steps of:
   (a) providing a first plural lumen catheter having an endoluminal sheath, a first lumen with optics and a second lumen, said sheath being radially non-collapsible and sufficiently axially rigid for positioning in a relatively large main vessel;
   (b) positioning the distal end of the first catheter adjacent the juncture of a relatively small branch vessel with the relatively large main vessel under the view provided by the optics in the first lumen of the first catheter;
   (c) providing a second plural lumen catheter having an endoluminal sheath, a first lumen with optics and a second lumen for a surgical instrument, the sheath of the second catheter being radially non-collapsible and sufficiently axially rigid for positioning the second catheter through the second lumen of the first catheter;
   (d) positioning the distal end of the second catheter into the relatively small branch vessel under the view provided by the optics in the first lumen of the second catheter;
   (e) inserting a surgical instrument through the second lumen in the second catheter into the branch vessel; and
   (f) performing a surgical procedure with the surgical instrument in the second lumen of the second catheter under the view provided by the optics in the first lumen of the second catheter.

12. An elongated, generally tubular, multilumen surgical catheter comprising in cross-section:
   a flexible outer sheath of generally circular cross-section;
   a central tube defining a generally cylindrical lumen connected to the interior wall of said outer sheath by rigid connection members, said tube, said rigid connection members, and said sheath defining plural peripheral lumens extending to the distal end of the catheter.

13. The multilumen catheter of claim 12 wherein at least one of said peripheral lumens is generally circular in cross-section.

14. An elongated, generally tubular, multilumen surgical catheter comprising in cross-section:
   a flexible outer sheath of generally circular cross-section;
   at least one tube defining a generally cylindrical lumen positioned interiorly of said sheath;
   a plurality of dividers,
   each of said plurality of dividers rigidly connected at one end to the exterior wall of said at least one tube and at the other end to the interior wall of said sheath to thereby define plural axial passageways isolated from each of said lumens and each of the other of said plural passageways.

15. The multilumen catheter of claim 14 wherein said tube is generally coaxial with said sheath.

16. The multilumen catheter of claim 14 wherein said at least one tube is two; and further including a divider rigidly connected to the exterior wall of said two tubes.

* * * * *